United States Patent
Kessler et al.

(10) Patent No.: US 7,147,620 B2
(45) Date of Patent: *Dec. 12, 2006

(54) ADAPTER FOR A PEG PROBE

(75) Inventors: Barbara Kessler, Kronberg (DE); Markus Schumacher, Aachen (DE); Barbara Breuer-Thal, Hattersheim (DE); Viktor Krütten, Hünstetten (DE)

(73) Assignee: Fresenius Kabi Deutschland GmbH (Company), Bad Homburg (DE)

( * ) Notice: Subject to any disclaimer, the term of this patent is extended or adjusted under 35 U.S.C. 154(b) by 457 days.

This patent is subject to a terminal disclaimer.

(21) Appl. No.: 10/431,226

(22) Filed: May 7, 2003

(65) Prior Publication Data
US 2003/0216713 A1 Nov. 20, 2003

Related U.S. Application Data

(63) Continuation of application No. PCT/EP01/12754, filed on Nov. 3, 2001.

(51) Int. Cl.
A61M 29/00 (2006.01)
A61M 25/16 (2006.01)

(52) U.S. Cl. .................. 604/104; 604/910; 604/539

(58) Field of Classification Search ........ 604/174–175, 604/264, 523, 537–539, 270, 910, 104; 606/108; 128/DIG. 6, 26
See application file for complete search history.

(56) References Cited

U.S. PATENT DOCUMENTS

| | | | | |
|---|---|---|---|---|
| 4,315,513 A * | 2/1982 | Nawash et al. ............ 604/537 |
| 4,393,873 A * | 7/1983 | Nawash et al. ............ 604/151 |
| 4,804,369 A * | 2/1989 | Lapeyre et al. ............ 604/175 |
| 5,267,969 A * | 12/1993 | Hirsch et al. ............. 604/174 |
| 5,314,411 A | 5/1994 | Bierman et al. ........... 604/174 |
| 5,342,321 A * | 8/1994 | Potter ...................... 604/174 |
| 5,374,254 A * | 12/1994 | Buma ....................... 604/175 |
| 5,527,280 A * | 6/1996 | Goelz ..................... 604/99.02 |
| 5,549,657 A * | 8/1996 | Stern et al. ............... 604/537 |
| 5,720,734 A * | 2/1998 | Copenhaver et al. ....... 604/247 |
| 5,836,924 A * | 11/1998 | Kelliher et al. ............ 604/248 |
| 5,947,931 A | 9/1999 | Bierman .................... 604/180 |
| 6,019,746 A * | 2/2000 | Picha et al. ................ 604/175 |
| 6,077,243 A * | 6/2000 | Quinn ..................... 604/93.01 |
| 6,458,106 B1 * | 10/2002 | Meier et al. ............... 604/264 |
| 6,482,183 B1 * | 11/2002 | Pausch et al. ............. 604/174 |
| 2004/0193115 A1 * | 9/2004 | Itrich et al. ................ 604/175 |

FOREIGN PATENT DOCUMENTS

DE 195 33 749 A1 9/1995
DE 197 21 372 A1 5/1997

(Continued)

Primary Examiner—LoAn H. Thanh
(74) Attorney, Agent, or Firm—Heslin Rothenberg Farley & Mesiti P.C.; Jeff Rothenberg, Esq.

(57) ABSTRACT

An adapter is connected to a probe tube of an already installed PEG probe, cut off above the abdominal wall of the patient. The adapter comprises a retaining member, supported by the abdominal wall, structure for fixing the proximal end of the PEG probe and structure for connecting a delivery tube. The retaining member is embodied as a separate piece, comprising an opening for the passage of the PEG probe, while the structures for fixing the PEG probe and for connection of the delivery tube form an insert piece, which may be inserted in the retaining member with a tight fit. The adapter is simple to manipulate and of a construction with a limited height.

13 Claims, 3 Drawing Sheets

FOREIGN PATENT DOCUMENTS

| | | |
|---|---|---|
| DE | 197 49 741 C1 | 11/1997 |
| EP | 0 824 929 A2 | 2/1998 |
| WO | WO 99/25414 | 5/1999 |
| WO | WO 99/55409 | 11/1999 |
| WO | WO 00/48658 | 8/2000 |

* cited by examiner

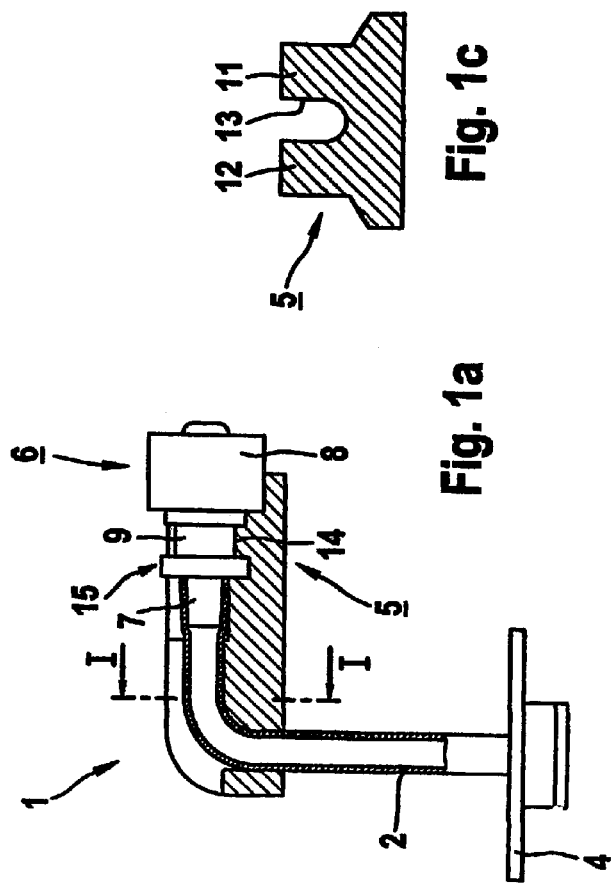
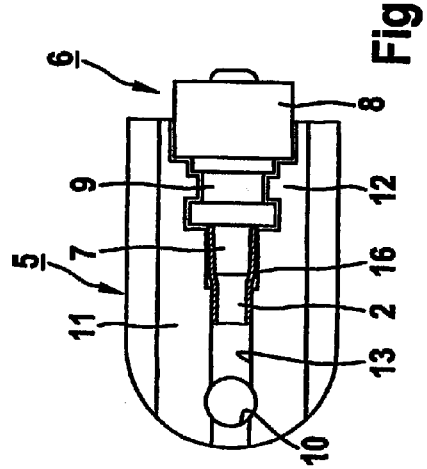
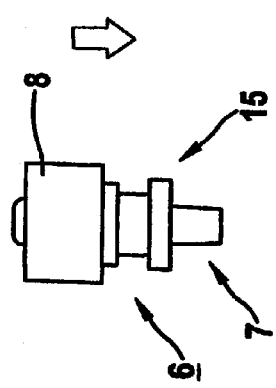

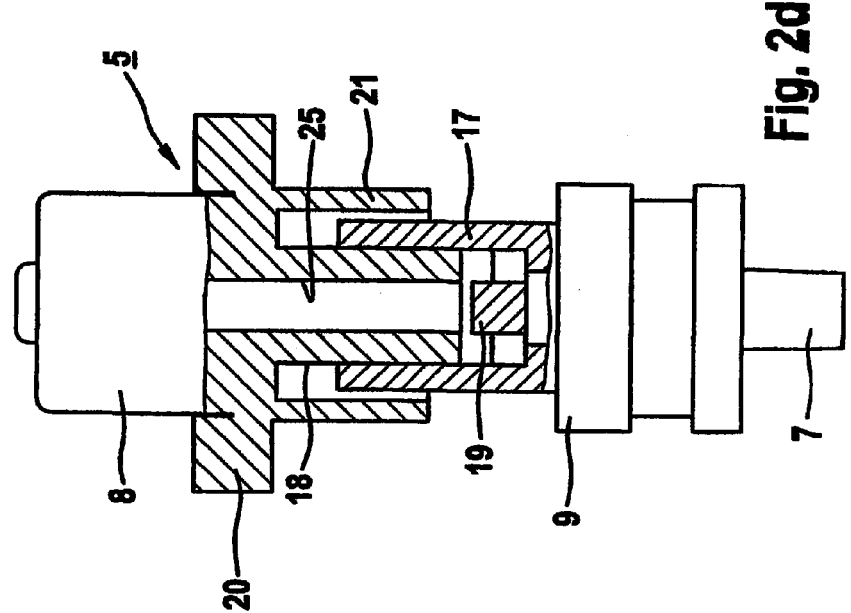
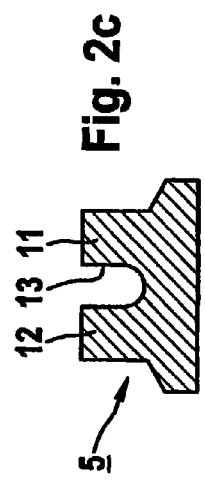
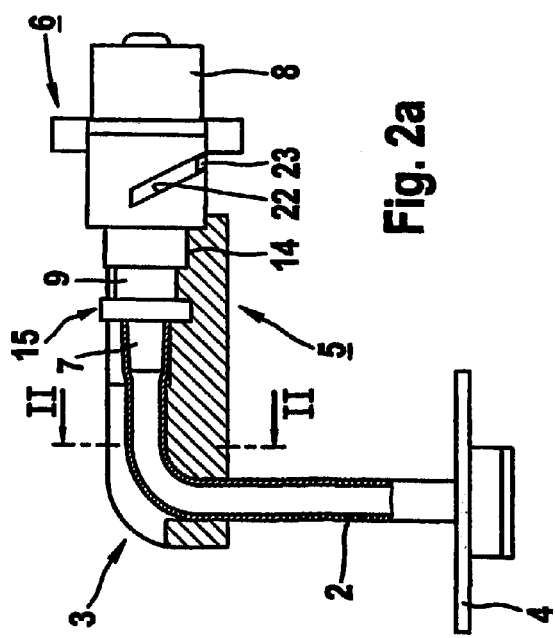
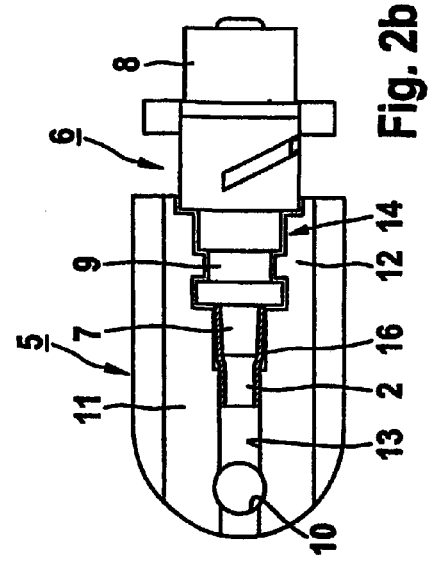

ADAPTER FOR A PEG PROBE

CROSS REFERENCE TO RELATED APPLICATIONS

This application is a continuation of international application PCT/EP01/12754 filed Nov. 3, 2001 and published in German as WO 02/38212 A1 on May 16, 2002, and claims priority from German application 10055281.1 filed Nov. 8, 2000, the entire contents of these applications being incorporated by reference herein. This application is also related to commonly assigned, concurrently filed U.S. application Ser. No. 10/431,034

BACKGROUND OF THE INVENTION

1. Field of the Invention

The invention relates to an adapter for subsequent shortening of a PEG probe which has already been put in place for artificial feeding.

2. Description of the Related Art

A PEG probe is fitted by introducing an endoscope or gastroscope into the patient's stomach and opening the stomach out by insufflation of air. A cannula is then advanced through the abdominal wall and stomach wall into the stomach lumen. A guide wire is introduced through the cannula into the stomach lumen, it is gripped with the endoscope or gastroscope and pulled back out through the patient's esophagus and mouth. With the aid of the guide wire which has been fitted in this way, the probe is then guided to the interior of the stomach and from there outward via the cannula. This procedure is also referred to as percutaneaus endoscopic gastrostomy (PEG).

At their distal end, the known PEG probes generally used have an inner retaining member with which the probe tube bears on the inner wall of the stomach. The probe tube is dimensioned so that it extends far out from the abdominal wall. At its proximal end the tube has a connection part in order to be able to connect the system far delivering nutrient solution. To close the probe tube, a conventional tube clamp or integrated closure cap is also often provided.

The known PEG probes have proven themselves in practice. However, a problem experienced by active patients is the fact that the probe tube protrudes relatively far out.

U.S. Pat. No. 5,549,657 describes a PEG probe which has an adapter for connection of a delivery system. The adapter is pushed on to the tube of the PEG probe and locked in place by means of a clamp. A disadvantage is that the probe tube has to be cut off immediately above the abdominal wall and has to be shortened exactly to the correct length. If the probe tube is cut too short, the adapter can no longer be secured, meaning that a new PEG probe has to be fitted. By contrast, if the probe tube is too long, the adapter does not lie on the abdominal wall. Furthermore, securing the adapter on the probe tube cut off just a short distance above the abdominal wall is relatively difficult.

The adapter is closed off by a slotted valve which opens upon connection of the delivery system. To open the valve, the connection part of the delivery system has a protruding cannula which is inserted into the adapter. For this reason, the known PEG probe is not directly compatible with the conventional delivery systems which have a Luer lock connector. In addition, there is a risk that the Y-shaped slotted valve does not provide a complete seal and too quickly loses its ability to function.

DE 197 49 741 C1 describes a fixing device for securing a PEG probe which has a support plate. The support plate has a recess for passage of the probe and a clamp part. To clamp the probe with the clamp part, the probe tube is bent through 90° above the abdominal wall. The known fixing device does not have means for connection of the probe tube of the PEG probe or a delivery tube of a delivery system.

WO 00/48658 describes a PEG probe with an inner retaining member located at its distal end and bearing on the stomach wall, and with a connection piece at its proximal end. To fix the probe on the abdominal wall of the patient, an outer retaining member is provided which has an opening for passage of the probe tube. The probe tube extends through the outer retaining member. The probe tube protrudes relatively far out from the abdominal wall, which is a disadvantage.

WO 99/25414, WO 99/55409 and U.S. Pat. No. 5,947,931 disclose securing systems for probe tubes on the patient's body. These securing systems, however, are not designed for shortening the probe tube of a PEG probe.

SUMMARY OF THE INVENTION

The object of the invention is to make available an easy-to-use adapter assembly (hereinafter sometimes referred to simply as "an adapter") with a low structural height with which it is possible to subsequently shorten the probe tube of an already fined PEG probe.

The adapter according to the invention permits shortening of the probe tube of an already fitted PEG probe without the need to change the probe with the catheter tube still intact, the adapter being connected to the catheter tube cut off above the abdominal wall.

The retaining member of the adapter according to the invention is designed as a separate part which has an opening for passage of the probe tube of the PEG probe. The means for securing the proximal end of the probe tube and the means for connection of the delivery tube form an insert piece which can be inserted into the retaining member.

To connect the adapter, the probe tube is shortened to the required length, but said probe tube does not have to be cut off directly above the abdominal wall. The protruding tube section is then guided through the opening of the retaining member, and said retaining member is placed on the abdominal wall. Only now is the probe tube connected, which is relatively easy on account of the adequate tube length. The insert piece is then inserted into the retaining member so that the adapter has only a low structural height.

To ensure that the insert piece is fixed adequately in the retaining member, the retaining member preferably has a profiled receiving portion and the insert piece has a correspondingly shaped insert portion which can be inserted with a tight fit into the receiving portion. The insert piece can be fixed by being clamped in the retaining member or only loosely inserted into it. If the insert piece lies only loosely in the retaining member, the fixing can be done via the probe tube. Such fixing is generally sufficient, although clamp brackets or the like can be provided to lock the insert piece in place.

In a preferred embodiment, the retaining member has a guide channel for the probe tube, which guide channel adjoins the opening and merges into the receiving portion. If the probe tube is guided through the opening of the retaining member and bent through 90°, a particularly flat profile can be obtained, although the tube is not cut off directly above the abdominal wall since the guide channel receives the protruding tube section. To be able to clamp the probe tube on the adapter, the receiving portion or guide channel of the retaining member preferably comprises a clamp portion. The clamp portion serves not simply to fix the probe tube by clamping, but also can secure the entire insert piece securely in the retaining member. The guide channel also reduces the risk of kinking of the probe tube at the bend point.

In a further preferred embodiment, the insert piece can be inserted in different positions into the retaining member so that the retaining member can receive different tube lengths. This is of advantage as the probe tube does not have to be cut off exactly to the required length.

The retaining member of the adapter bearing on the abdominal wall should be made of a conformable elastic material, for example silicone rubber with especially good biocompatibility properties, while the other parts of the adapter should be made from shape-stable materials, for example thermoplastics, in order to give the adapter the necessary stability. The retaining member is preferably designed as a plate-shaped body so that the adapter has the lowest possible structural height.

To close the adapter, a shutoff member with a rotatable or displaceable closure body is provided. The shut-off member is of advantage because the delivery system does not need to have a special attachment part which opens the adapter upon connection. For this reason, it is in principle possible to attach all application systems for enteral nutrition which have different attachment parts.

The closure body of the shut-off member can be a cylinder body which is mounted so as to be able to rotate and which is closed off at one end and open at the other end and is provided with a transverse bore. When the closure body opens the shut-off member, fluid can flow out of the flow channel of the adapter through the transverse bore and into the cylinder body. This closure body makes it possible to arrange the Luer lock connector transversely with respect to the flow channel, by which means a particularly low structural height of the adapter is achieved and a lateral attachment of the delivery tube is possible.

The closure body can also be a valve piece which is pushed axially into the flow channel. This embodiment is of advantage if the Luer lock connector is to be arranged in the longitudinal direction of the flow channel, i.e. the delivery tube is not closed off laterally.

To simplify handling, the closure piece can be displaced by rotating the outer housing body of the adapter. The conversion of the rotation movement to a translation movement is preferably effected by means of a guide track.

Since the shut-off member closes the adapter tightly, it is in principle possible to dispense with an additional closure cap. However, this is of advantage as it protects the Luer lock connector of the adapter.

In a preferred embodiment, the adapter for connection of the delivery tube has a Luer lock connector which is distinguished by a low structural height and secure connection.

BRIEF DESCRIPTION OF THE DRAWINGS

A number of illustrative embodiments of the invention will be described in more detail below with reference to the drawings, in which:

FIG. 1a shows, in partial cross section, a first embodiment of the adapter connected to a PEG probe, FIG. 1b shows the adapter from FIG. 1a in plan view, FIG. 1c shows a section through the adapter along line I—I in FIG. 1a, FIG. 1d shows an exploded view of the adapter from FIG. 1a, FIG. 2a shows a second illustrative embodiment of the adapter connected to the PEG probe, FIG. 2b shows the adapter from FIG. 2a in plan view, FIG. 2c shows a section through the adapter along line II—II in FIG. 2a, FIG. 2d shows, in partial cross section, the insert piece of the adapter from FIG. 2a, which insert piece can be inserted into the retaining member.

DETAILED DESCRIPTION

Figure 3:
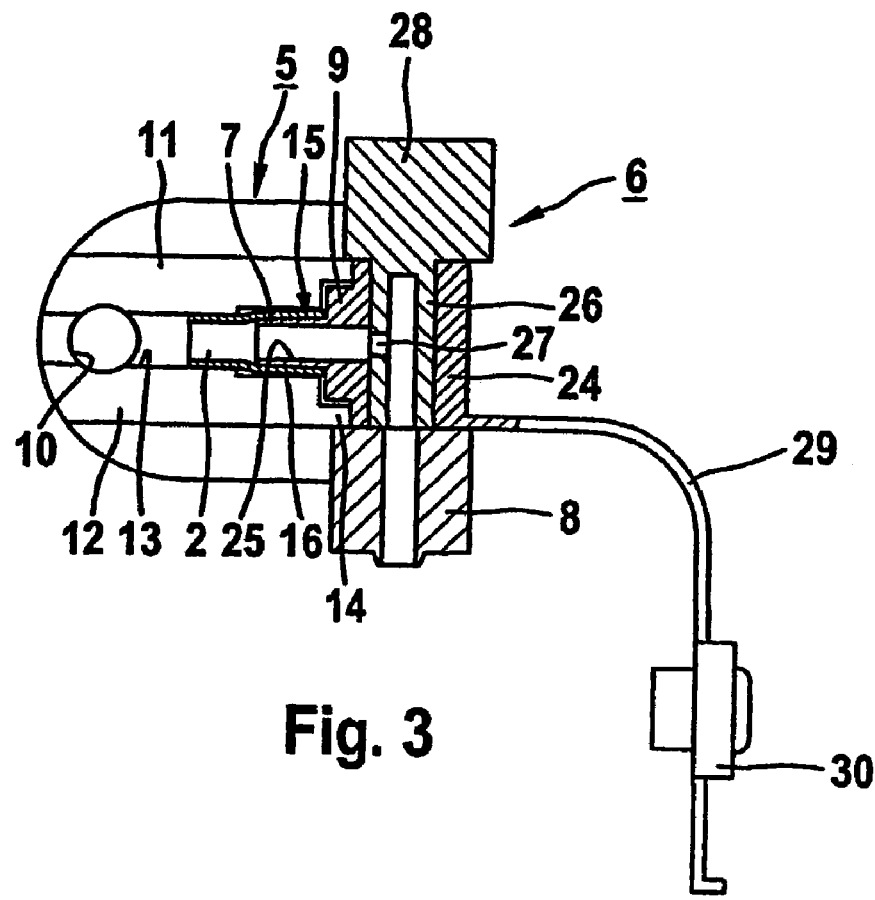
FIG. 3 shows a further illustrative embodiment of the adapter in partial cross section.

FIGS. 1a through 1d show a first embodiment of the adapter assembly or adapter 1 for the probe tube 2 of a PEG probe 3. At its distal end, the probe tube 2 of the PEG probe 3 has a plate-shaped inner retaining member 4 with which the tube bears on the stomach wall. The outer retaining member 5, with which the PEG probe bears on the abdominal wall, is a component part of the adapter.

The adapter consists of the plate-shaped, elongate retaining member 5, which is designed as a separate part, and of an insert piece 6 with the means 7 for securing the proximal end of the probe tube 2 and the means 8 for connecting the delivery tube of a delivery system (not shown).

For the means 8 for connection of the delivery tube, the insert piece 6 has a male Luer lock connector. Adjoining the Luer lock connector 8 there is a cylindrical base part 9 which has a reduced diameter at its center. The cylindrical base part 9 merges into a conical hollow stub onto which the proximal end of the probe tube 2 is pushed and which serves as the means 7 for securing the proximal end of the probe tube.

The retaining member 5 has an opening 10 for passage of the probe tube, said, opening 10 being adjoined by a guide channel 13 delimited by two parallel webs 11, 12 for the tube line 2, which extends in the longitudinal direction of the retaining member. The guide channel 13 merges into a profiled receiving portion 14 into which it is possible to fit a correspondingly profiled insert portion 15 of the insert piece 6 which is formed by the base part 9 and by part of the Luer lock connector 8.

The profiled receiving portion 14 of the retaining member 5 has a rear clamp portion 16 which is so dimensioned that the probe tube pushed onto the hollow stub 7 of the base part 9 is fixed by clamping when the insert piece 6 of the adapter is inserted.

To connect the adapter, the probe tube 2 is guided through the opening 10, cut to the correct length and pushed onto the hollow stub 7 of the insert piece 6. The probe tube is then bent through 90° and fitted into the guide channel, and the insert piece is inserted with its profiled insert portion 15 into the profiled receiving portion 14 of the retaining member 5. To reduce the risk of kinking , the retaining member is rounded in the area of the tube bend. The connection is relieved by clamping the tube in the clamp portion. The positive connection of insert piece and retaining member affords further stability.

The delivery tube (not shown) of the delivery system has a female Luer lock connector. To connect the delivery tube, the two Luer lock connectors of the adapter and tube are connected to one another.

The areas of the retaining member 5 with direct skin and tissue contact consist of a conformable, biocompatible material, for example silicone rubber, whereas the other parts of the retaining member are made of harder materials, for example thermoplastics.

FIGS. 2a through 2d show a second illustrative embodiment of the adapter which differs from the embodiment according to FIGS. 1a through 1d in that the adapter can be closed. The parts of the illustrative embodiment according to FIGS. 2a through 2d which correspond to the parts of the embodiment according to FIGS. 1a through 1d are provided with the same reference numbers.

The adapter once again has a separate retaining member 5 and an insert piece 6. FIG. 2d shows the insert piece of this embodiment in partial cross section. The insert piece has a closure member between the Luer lock connector 8 and the base part 9. The base part 9 merges into a first hollow cylindrical body 17 in which a second hollow cylindrical body 18 is guided in a longitudinally displaceable manner. A cylindrical closure piece 19 is arranged concentrically in the first cylinder body 17. The Luer lock connector adjoins the second cylinder body 18.

Provided on the underside of the Luer lock connector 8 there is an annular attachment 20 from which there extends a sleeve-shaped body 21 which has a guide track 22 for a guide pin 23 extending radially outward from the first cylinder body 17 (FIG. 2a).

To close the PEG probe 3, the upper part of the insert piece 6 is turned so that the first and second cylinder bodies 17, 18 are pushed together, as a result of which the cylindrical closure piece 9 is guided sealingly into the flow channel 25 of the second cylinder body 18. The annular attachment 25 can be provided with knurling or the like to permit better gripping of the insert piece 6.

FIG. 3 shows a further illustrative embodiment of the adapter in partial cross section. The parts corresponding to one another are again provided with the same reference numbers.

The insert piece 6 again has a base part 9 with a hollow stub 7 onto which the probe tube 2 is pushed. Adjoining the base part 9 is the housing body 24 of the shut-off member in which a hollow cylindrical shut-off body 26 is rotatably mounted transverse to the longitudinal axis of the flow channel 25, which shut-off body 26 is open at one end, closed at the other end and provided with a central transverse bore 27. The cylinder body 26 can be turned by means of an adjusting screw 28 which is integral with the cylinder body. Before the open end of the cylinder body 26, the Luer lock connector 8 is attached to the housing body 24. The adapter is opened/closed by turning the closure body 26 via the adjusting screw 28. A flexible tab 29 is secured on the side of the housing body 24, on which tab 29 a closure cap 30 is arranged for closing the Luer lock connector 8.

The retaining member 5 differs from the retaining member according to FIGS. 2a through 2d only in that the receiving portion 14 has a profile corresponding to the insert portion 15 of the insert piece 6. The receiving portion 14 is profiled in such a way that the insert piece 6 bears with the adjusting screw 28 and the Luer lock connector 8 on the side of the retaining member. Otherwise, the retaining member corresponds to the retaining member according to FIGS. 2a through 2d.

Figure 4:
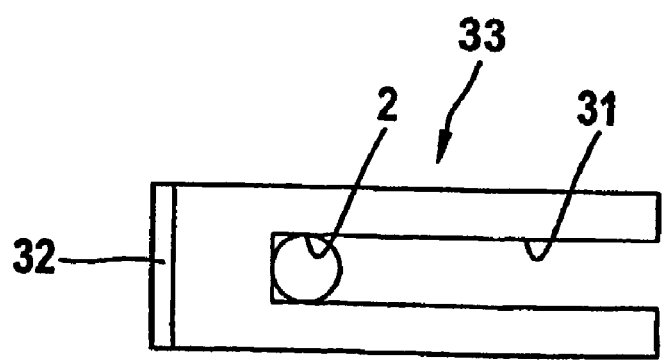
FIG. 4 shows a fixing element for the probe tube.

FIG. 4 shows a fixing element 33 for the probe tube 2 of the PEG probe. The fixing element is designed as a flat plate which is indented in the longitudinal direction. The indent 31 has, a smaller width than the probe tube, so that the tube can, be clamped with the fixing element. The thickness of the fixing element corresponds to the desired spacing between abdominal wall and the outer retaining member 5 of the adapter. At the edge lying opposite the indent, the fixing element has a projecting attachment 32. To fit the PEG probe, the fixing element is placed on the abdominal wall and pushed laterally onto the probe tube until the limit stop 32 strikes against the retaining member, so that the tube is fixed by clamping. The probe tube is then cut off, and the retaining member is pushed onto the probe tube and the connection part is secured. The fixing element here serves as a spacer.

What is claimed is:

1. An adapter assembly for a PEG probe, said probe having a flexible probe tube with an inner retaining member located at a distal end and adaptable on a stomach wall, and with an open proximal end, said adapter assembly comprising:

an outer retaining member adaptable on an abdominal wall, means for securing the proximal end of the probe tube with a section of said flexible probe tube protruding beyond the abdominal wall, and means for connection of a delivery tube, said outer retaining member comprising a part separate from said probe which has an opening for passage of the protruding probe tube section, wherein the means for securing the proximal end of the probe tube and the means for connection of the delivery tube form an insert piece, the outer retaining member being configured such that the insert piece can be inserted into a receiving portion of the outer retaining member, and wherein the outer retaining member has a guide channel for the protruding probe tube section, which guide channel adjoins the opening, guides the protruding probe tube section through a bend, and merges into the receiving portion.

2. The adapter assembly as claimed in claim 1, wherein the outer retaining member has a profiled receiving portion and the insert piece has a correspondingly profiled insert portion which can be inserted into the receiving portion with a tight fit.

3. The adapter assembly as claimed in claim 1, wherein a base portion of the guide channel is rounded in an area of the bend to reduce risk of tube kinking.

4. The adapter assembly as claimed in claim 1, wherein the receiving portion of the outer retaining member comprises a clamp portion in which the probe tube can be clamped fixed.

5. The adapter assembly as claimed in claim 1, wherein the outer retaining member comprises a plate-shaped body.

6. An adapter assembly for a PEG probe, said probe having a flexible probe tube with an inner retaining member located at a distal end and adaptable on a stomach wall, and with an open proximal end, said adapter assembly comprising:

an outer retaining member adaptable on an abdominal wall, means for securing the proximal end of the probe tube with a section of said flexible probe tube protruding beyond the abdominal wall, and means for connection of a delivery tube, said outer retaining member comprising a part separate from said probe which has an opening for passage of the protruding probe tube section, wherein the means for securing the proximal end of the probe tube and the means for connection of the delivery tube form an insert piece, the outer retaining member being configured such that the insert piece can be inserted into a receiving portion of the outer retaining member, wherein the outer retaining member has a guide channel for the protruding probe tube section, which guide channel adjoins the opening and merges into the receiving portion, and wherein the means for connection of the delivery tube is a Luer lock connector.

7. The adapter assembly as claimed in claim 6, wherein the Luer lock connector can be closed with a closure cap.

8. An adapter assembly for a PEG probe, said probe having a flexible probe tube with an inner retaining member located at a distal end and adaptable on a stomach wall, and with an open proximal end, said adapter assembly comprising:

an outer retaining member adaptable on an abdominal wall, means for securing the proximal end of the probe tube with a section of said flexible probe tube protruding beyond the abdominal wall, and means for connection of a delivery tube, said outer retaining member comprising a part separate from said probe which has an opening for passage of the protruding probe tube section, wherein the means for securing the proximal end of the probe tube and the means for connection of the delivery tube form an insert piece, the outer retaining member being configured such that the insert piece can be inserted into a receiving portion of the outer retaining member, wherein the outer retaining member has a guide channel for the protruding probe tube section, which guide channel adjoins the opening and merges into the receiving portion. and further comprising a shut-off member with a rotatable or displaceable closure body, with which a flow channel in the adapter assembly can be closed off.

9. The adapter assembly as claimed in claim 8, wherein the closure body is a cylinder body which is mounted so as to be able to rotate and which is closed at one end and open at another end and is provided with a transverse bore, the means for securing the delivery tube being arranged at the open end of the closure body.

10. The adapter assembly as claimed in claim 8, wherein the closure body is a cylindrical closure piece which can be pushed axially into the flow channel.

11. The adapter assembly as claimed in claim 10, wherein the cylindrical closure piece is arranged concentrically in a first cylinder body, and a second cylinder body is inserted into the first cylinder body, said first and second cylinder bodies being displaceable relative to one another by a guide.

12. An adapter assembly for a PEG probe, said probe having a flexible probe tube with an inner retaining member located at a distal end and adaptable on a stomach wall, and with an open proximal end, said adapter assembly comprising:

an outer retaining member adaptable on an abdominal wall, means for securing the proximal end of the probe tube with a section of said flexible probe tube protruding beyond the abdominal wall, and means for connection of a delivery tube, said outer retaining member comprising a part separate from said probe which has an opening for passage of the protruding probe tube section, wherein the means for securing the proximal end of the probe tube and the means for connection of the delivery tube form an insert piece, the outer retaining member being configured such that the insert piece can be inserted into a receiving portion of the outer retaining member, wherein the outer retaining member has a guide channel for the protruding probe tube section, which guide channel adjoins the opening and merges into the receiving portion, and further including a fixing element for fixing the protruding probe tube section by clamping, which fixing element comprises a small flat plate with a lateral indent.

13. The adapter assembly as claimed in claim 3, wherein the bend comprises a 90° bend.

* * * * *